United States Patent [19]

Bianchetti et al.

[11] Patent Number: 5,026,716
[45] Date of Patent: Jun. 25, 1991

[54] METHOD OF TREATMENT OF ANXIETY AND ANXIO-DEPRESSIVE DISORDERS

[75] Inventors: Alberto Bianchetti, Milan, Italy; Gérard Le Fur, Montmorency, France; Jacques Simiand, Muret, France; Philippe Soubrie, Saint-Mathieu de Treviers, France

[73] Assignee: Sanofi, France

[21] Appl. No.: 437,674

[22] Filed: Nov. 17, 1989

[30] Foreign Application Priority Data

Nov. 18, 1988 [FR] France ............... 88 15036

[51] Int. Cl.$^5$ ............... A01H 43/40; C07D 499/46
[52] U.S. Cl. ............... 514/336; 514/277; 514/357; 540/330
[58] Field of Search ............... 514/336, 277

[56] References Cited

U.S. PATENT DOCUMENTS

| | | | |
|---|---|---|---|
| 4,472,408 | 9/1984 | Nisato et al. | 424/263 |
| 4,521,428 | 6/1985 | Nisato et al. | 514/277 |
| 4,602,024 | 7/1986 | Nisato et al. | 514/357 |
| 4,691,019 | 9/1987 | Nisato et al. | 540/330 |

OTHER PUBLICATIONS

Chem. Abst. 101-7038f (1984).

Primary Examiner—Stanley J. Friedman
Assistant Examiner—Theodore J. Criares
Attorney, Agent, or Firm—Bacon & Thomas

[57] ABSTRACT

A method of treatment of anxiety and depression in mammals is described which comprises administering to a mammal in need thereof an effective amount of a trifluoromethylphenyl-tetrahydropyridine derivative of formula I

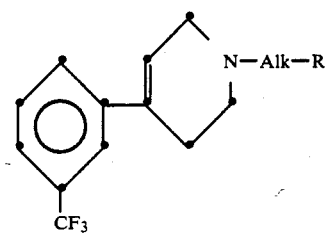

wherein Alk represents a straight or branched ($C_1$-$C_4$)alkylene chain and R is selected from the group consisting of cyano, acetyl, ($C_3$-$C_7$)cycloalkyl, pyridyl, 1-oxide-pyridyl and naphthyl, or of a pharmaceutically acceptable salt thereof.

7 Claims, No Drawings

METHOD OF TREATMENT OF ANXIETY AND ANXIO-DEPRESSIVE DISORDERS

DISCLOSURE OF THE INVENTION

The present invention refers to a method of treatment of anxiety and anxio-depressive disorders in mammals which comprises administering to a mammal in need thereof an effective amount of a trifluoromethylphenyl-tetrahydropyridine of general formula I

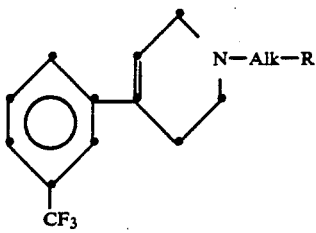

wherein Alk represents a straight or branched ($C_1-C_4$)alkylene chain and R is a radical selected from the group consisting of cyano, acetyl, ($C_3-C_7$)cycloalkyl, pyridyl, 1-oxide-pyridyl and naphthyl, or of a pharmaceutically acceptable salt thereof.

European patents 60,176 and 101,381 describe some N-substituted trifluoromethylphenyl-tetrahydropyridines with anorectic activity.

It has now been found that said trifluoromethylphenyl-tetrahydropyridines have a good anxiolytic and antidepressant activity.

It has also been found that the anxiolytic activity of said compounds is not accompanied, at anxiolytically effective doses, by a sedative effect, and that the anxiolytic and antidepressant activities are elicited at doses which are remarkably lower than those which produce anorexia.

A first object of the present invention is therefore a method of treatment of anxiety and anxio-depressive disorders in mammals which comprises administering to a mammal in need thereof an effective amount of a trifluoromethylphenyl-tetrahydropyridine derivative of formula I

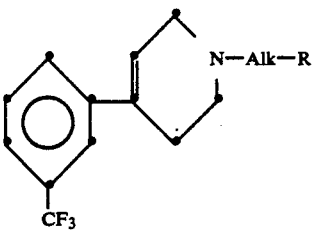

wherein Alk represents a straight or branched ($C_1-C_4$)alkylene chain and R is a radical selected from the group consisting of cyano, acetyl, ($C_3-C_7$)cycloalkyl, pyridyl, 1-oxide-pyridyl and naphthyl, or of a pharmaceutically acceptable salt thereof.

The term "pyridyl" for R identifies a 2-, 3-, or 4-pyridyl radical, while the term "naphthyl" designates a 1-naphthyl or 2-naphthyl radical.

For use in the method of the present invention, a preferred group of compounds comprises those compounds of formula I wherein Alk represents an ethylene group and R is 2-pyridyl, 4-pyridyl, 1-oxide-4-pyridyl, cyclohexyl, or 2-naphthyl. Another preferred group of compounds comprises those compounds of formula I wherein Alk is ethylene, propylene or butylene and R is cyano.

A most preferred compound is however the compound of formula I wherein Alk is ethylene and R is 2-naphthyl (i.e. 1- 2-(2-naphthyl)-ethyl -4-(3-trifluoromethylphenyl)-1,2,3,6-tetrahydropyridine) and its pharmaceutically acceptable salts, and particularly the hydrochloride, hereinafter indicated as SR 57746 A.

The compounds of formula I and the preparation thereof are described in EP-60,176 and EP-101,381. More particularly the compound indicated as SR 57746 A and its preparation are described in Example 7 of EP-101,381.

Among the above compounds, that of formula I wherein Alk is ethylene and H is a cyano group (which has been described in Examples 2 and 15 of EP 60,176 and has the Applicant's reference CM 57493) has been submitted to all the tests required to enter the clinical phase. It showed to be well tolerated and poorly toxic and substantially devoid of unwanted side-effects. Tested in the human at 80 and 160 mg, this product was well tolerated and favourably affected the mood.

The compounds of formula I which proved to be active, at very low doses, in a range of tests claimed to be models of anxiety and/or depression, are therefore useful for the treatment of anxiety and depression in mammals.

For the treatment of anxiety and depression in mammals the compounds of formula I can be administered orally, sub-lingually, transdermally or parenterally. The amount of active principle which has to be administered for the treatment of anxiety and depression will depend, as usual, on the type of treatment, whether prophylactic or curative, on the severity of the troubles to be treated, as well as on the weight of the patients and the rout of administration.

In human beings the dosage may vary from 0.2 to 150 mg per day, administered once to three times a day, the lower doses being suitable for children.

The compounds of formula I and their pharmaceutically acceptable salts are generally administered in unit dosage forms of from 0.2 to 150 mg, preferably of from 0.5 to 50 mg of active principle.

Said unit doses are formulated in pharmaceutical compositions in which the active ingredient of formula I is alone or preferably in admixture with a pharmaceutical carrier. The pharmaceutical compositions can be easily prepared according to the method known in industrial pharmacy and more particularly according to the methods already described in EP-60,176 and EP-101,381.

In particular, when a solid composition is prepared in the form of tablets, the main active ingredient is mixed with a pharmaceutical carrier such as gelatine, starch, lactose, magnesium stearate, talc, arabic gum and the like. The tablets may be coated with sucrose or other appropriate materials or they may be treated so that their activity is extended or delayed and that they continuously release a predetermined amount of active ingredient.

A preparation in capsules is obtained by mixing the active ingredient with a diluent and by pouring the mixture obtained in soft or hard capsules.

A preparation in the form of syrup or elixir may contain the active ingredient jointly with a possibly acaloric sweetening agent, methylparaben and propylparaben as antiseptics, as well as a flavoring agent and an appropriate dye.

Water-dispersible powders or granulates may contain the active ingredient mixed with dispersing agents or wetting agents, or suspending agents such as polyvinylpyrrolidone and the like, and with sweetening or flavoring agents as well.

The active ingredient may also be formulated in the form of microcapsules, possibly with one or more carriers or additives.

For sublingual administration microtablets or microcapsules can be prepared which placed under the tongue will rapidly dissolve. These compositions will generally contain the active ingredient in admixture with wetting and/or dispersing agents and optionally with absorption enhancers.

For transdermic administration the use of polymeric diffusion matrices for the continuous and preferably sustained release of the active principle can be devised as well as the use of the active principle as a microemulsion with excipients adapted for contact with the skin.

For parenteral administration, aqueous suspensions, isotonic saline solutions or sterile injectable solutions are used, which contain pharmacologically compatible dispersing and/or wetting agents, for example propyleneglycol or butyleneglycol.

Another object of the present invention is therefore a pharmaceutical composition useful for the treatment of anxiety and depression, said composition comprising a compound of formula I or a pharmaceutically acceptable salt thereof, as the active ingredient.

The following examples further illustrate the invention without however limiting it.

EXAMPLE 1

A representative compound of formula I, SH 57746 A, has been evaluated in the territorial aggressiveness (T.A.) test carried out in mice according to the method described by C. Y. Yen et Al. in Arch. Int. Pharmacodyn., 1959, 123, 179-185. In this test SR 57746 A showed to be active at 1 mg/kg p.o.. Furthermore, when administered at 3 mg/kg p.o., the pharmacological activity of SH 57746 A lasted longer than 7 hours.

EXAMPLE 2

A representative compound of formula I, SR 57746 A, has been evaluated in the Geller-Seifter Conflict (G-S.C.) test carried out in rats according to the method described by J. Geller et al. in Psychopharmacologia, Berlin, 1960, I, 482-492. SR 57746 A elicited an anxiolytic effect at a dose ten times lower than the sedative one. More particularly release of punished responses which is related to the anxiolytic activity was observed at doses as low as 3 mg/kg p.o., whereas reduction of the unpunished responses which correlates with the sedative activity was observed at 30 mg/kg p.o.. Anorectic activity in the rat is obtained at 10.4 mg/kg p.o.

EXAMPLE 3

SR 57746 A showed to be active also in a test which is specifically claimed to be a model of anxiety i.e. in the conditioned taste adversion test in rats and in particular in the lithium induced taste adversion test (L.A.) which has been performed according to the method described by G. N. Evin et al. in Drug Development Research. 1987, 11, 87-95. The minimal effective dose of SR 57746 A was 3 mg/kg p.o.

EXAMPLE 4

SR 57746 A was active also in a specific model of depression, i.e. the learned helplessness test which has been carried out in rats according to the method described by A. D. Sherman et al in Pharmacol. Biochem. Behav., 1982, 16, 449-454. The oral active dose was 0.5 mg/kg/day for 5 days and the elicited effect was identical to that obtained with an oral dose of 32 mg/kg/day of imipramine.

EXAMPLE 5

Tablets comprising 2 mg or 4 mg of SR 57746 A, as the free base, are prepared by using the ingredients of Example 11 of EP-101,381 in equivalent proportions. Analogously tablets comprising 2.5, 5 and 10 mg of active principle are prepared.

We claim:

1. A method of treatment of anxiety and anxiodepressive disorders in mammals which comprises administering to a mammal in need thereof an effective amount of a trifluoromethylphenyl-tetrahydropyridine of general formula I

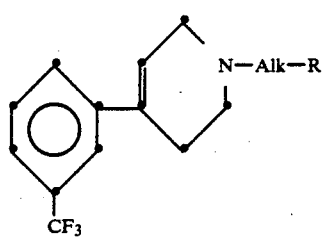

wherein Alk represents a straight or branched ($C_1$-$C_4$)alkylene chain and R is a radical selected from the group consisting of cyano, acetyl, ($C_3$-$C_7$)cycloalkyl, pyridyl, 1-oxide-pyridyl and naphthyl, or of a pharmaceutically acceptable salt thereof.

2. The method of treatment of claim 1, wherein in formula I Alk is ethylene and R represents a radical selected from the group consisting of 2-pyridyl, 4-pyridyl, 1-oxide-4-pyridyl, cyclohexyl and 2-naphthyl.

3. The method of treatment of claim 1, wherein in formula I Alk is ethylene, propylene, or butylene and R is cyano.

4. The method of treatment of claim 2, wherein R is 2-naphthyl.

5. The method of treatment of claim 4, which comprises administering an effective amount of 1-[2-(2-naphthyl)ethyl]-4-(3-trifluoromethylphenyl)-1,2,3,6-tetrahydropyridine hydrochloride.

6. The method of treatment of claim 1, wherein the effective amount is from 0.2 to 150 mg/day.

7. The method of treatment of claim 4, wherein the effective amount is divided in 2 or 3 doses.

* * * * *